US012758086B2

(12) United States Patent
Wang et al.

(10) Patent No.: US 12,758,086 B2
(45) Date of Patent: Oct. 13, 2026

(54) MAGNETIC BALL CALIBRATION METHOD AND MAGNETIC BALL CALIBRATION APPARATUS

(71) Applicant: Ankon Medical Technologies (Shanghai) Co., LTD, Shanghai (CN)

(72) Inventors: Tingqi Wang, Shanghai (CN); Xiaodong Duan, Plano, TX (US)

(73) Assignees: ANKON MEDICAL TECHNOLOGIES (SHANGHAI) CO., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 164 days.

(21) Appl. No.: 18/833,934

(22) PCT Filed: Jan. 16, 2023

(86) PCT No.: PCT/CN2023/072318
§ 371 (c)(1),
(2) Date: Jul. 29, 2024

(87) PCT Pub. No.: WO2023/143172
PCT Pub. Date: Aug. 3, 2023

(65) Prior Publication Data

US 2025/0113980 A1 Apr. 10, 2025

(30) Foreign Application Priority Data

Jan. 28, 2022 (CN) ......................... 202210104801.7

(51) Int. Cl.
*A61B 1/00* (2006.01)

(52) U.S. Cl.
CPC ...... *A61B 1/00158* (2013.01); *A61B 1/00057* (2013.01)

(58) Field of Classification Search
CPC . A61B 1/00057; A61B 1/00158; A61B 1/041; G01R 33/0206
See application file for complete search history.

(56) References Cited

U.S. PATENT DOCUMENTS

2002/0100486 A1* 8/2002 Creighton, IV ....... A61B 34/73 128/899
2005/0143648 A1 6/2005 Minai et al.
(Continued)

FOREIGN PATENT DOCUMENTS

CN 101382586 A 3/2009
CN 102053232 A 5/2011
(Continued)

*Primary Examiner* — Michael J Carey
*Assistant Examiner* — Stephen Floyd London
(74) *Attorney, Agent, or Firm* — Treasure IP Group, LLC

(57) ABSTRACT

The present application discloses a magnetic ball calibration method and a magnetic ball calibration apparatus. The method includes: rotating a magnetic ball around a first axis by a first angle, obtaining detection data during rotation, obtaining a zero point position $P_0$ with a magnetic field intensity component in the direction of a second axis being zero; obtaining a calibration position of the magnetic ball according to the detection data and the zero point position $P_0$; and calibrating the magnetic ball according to the calibration position of the magnetic ball; where when the magnetic ball is located at the calibration position, the magnetic polarization direction of the magnetic ball coincides with the second axis; the first axis is perpendicular to the second axis. By means of the magnetic ball calibration method and the magnetic ball calibration apparatus, the magnetic ball can be calibrated conveniently, quickly and accurately.

11 Claims, 5 Drawing Sheets

(56) References Cited

U.S. PATENT DOCUMENTS

| | | | | |
|---|---|---|---|---|
| 2007/0244388 | A1* | 10/2007 | Sato | A61B 1/041 600/550 |
| 2016/0066813 | A1* | 3/2016 | Kimchy | A61B 1/00004 600/409 |
| 2016/0258781 | A1 | 9/2016 | Ausserlechner et al. | |
| 2017/0156574 | A1* | 6/2017 | Kawano | A61B 1/00 |
| 2019/0301848 | A1* | 10/2019 | Aloui | G01B 7/31 |
| 2019/0320887 | A1* | 10/2019 | Shelton | A61B 1/00045 |
| 2019/0335983 | A1* | 11/2019 | Duan | G01R 33/0206 |
| 2020/0196844 | A1* | 6/2020 | Sitti | A61B 1/000096 |
| 2022/0248943 | A1* | 8/2022 | Peng | A61B 5/073 |

FOREIGN PATENT DOCUMENTS

| | | | |
|---|---|---|---|
| CN | 106569150 | A | 4/2017 |
| CN | 107179093 | A | 9/2017 |
| CN | 109716168 | A | 5/2019 |
| CN | 109831135 | A | 5/2019 |
| CN | 111707175 | A | 9/2020 |
| CN | 111707296 | A | 9/2020 |
| CN | 112344968 | A | 2/2021 |
| JP | H07244143 | A | 9/1995 |
| JP | 2016050841 | A | 4/2016 |

* cited by examiner

MAGNETIC BALL CALIBRATION METHOD AND MAGNETIC BALL CALIBRATION APPARATUS

CROSS-REFERENCE OF RELATED APPLICATIONS

The application is a National Phase Application of PCT International Application No. PCT/CN2023/072318, International Filing Date Jan. 16, 2023, published Aug. 3, 2023 as International Publication Number WO2023/143172A1, which claims priority from Chinese Patent Application No. 202210104801.7, filed Jan. 28, 2022, all of which are incorporated herein by reference in their entirety.

FIELD OF INVENTION

The present application relates to a magnetic control technique and a capsule endoscope technique, and more particularly to a magnetic ball calibration method and a magnetic ball calibration apparatus.

BACKGROUND

Capsule endoscopes, which can be actively controlled by external magnetic control devices, provide detailed and comprehensive examinations. Compared to traditional endoscopes, capsule endoscopes offer the advantages of better comfort and lower risk of cross-infection, leading to their increased adoption in clinical applications.

For a magnetically controlled capsule endoscope system, the permanent magnet (usually a magnetic sphere, i.e., magnetic ball) on the external magnetic control device is the core component for controlling the movement of the capsule endoscope. By controlling the attitude and/or position of the magnetic ball, the magnetic field changes, enabling the capsule endoscope to achieve corresponding movements such as translation, rotation, and flip according to the changed magnetic field. The magnetic ball influences the attitude of the capsule endoscope through the direction of the magnetic field. In practical use, uncertainties in the magnetic field direction or deviations in the position of the magnetic poles of the permanent magnet can cause significant errors in the attitude angle of the capsule endoscope, affecting the precision of the attitude of the capsule endoscope and, consequently, the accuracy of the information acquisition of the capsule endoscope. For the external magnetic control device of the capsule endoscope, it is necessary to calibrate the direction of the magnetic ball during use.

In the prior art, multiple sensors are typically used to obtain magnetic field data to determine the magnetic field direction of the magnetic ball. Although this method can accurately determine the magnetic field direction of the magnetic ball, the process is cumbersome and the operation is complex, which is not conducive to widespread application.

Therefore, there is a need for a simpler, more convenient, and accurate magnetic ball calibration method and magnetic ball calibration apparatus.

SUMMARY OF THE INVENTION

In view of the above problems, the object of the present application is to provide a magnetic ball calibration method and a magnetic ball calibration apparatus, so as to accurately, conveniently, and quickly calibrate the magnetic ball.

According to one aspect of the present application, a magnetic ball calibration method is provided, comprising the following steps:

- rotating the magnetic ball around a first axis by a first angle, and obtaining detection data of the three-axis magnetic field components at a detection position during rotation, wherein the first angle is greater than or equal to 180°;
- obtaining a zero point position $P_0$ of the magnetic ball with a magnetic field intensity component in the direction of a second axis being zero according to the detection data;
- obtaining a calibration position of the magnetic ball according to the detection data and the zero point position $P_0$;
- calibrating the magnetic ball according to the calibration position of the magnetic ball;
- wherein, when the magnetic ball is located at the calibration position, the magnetic polarization direction of the magnetic ball coincides with the second axis;
- the first axis is perpendicular to the second axis;
- the three-axis magnetic field components comprise an X-axis magnetic field component, a Y-axis magnetic field component and a Z-axis magnetic field component;
- the direction of the Z-axis magnetic field component coincides with the direction of the second axis, and the direction of the Y-axis magnetic field component coincides with that of the first axis.

Preferably, obtaining a zero point position $P_0$ of the magnetic ball with a magnetic field intensity component in the direction of a second axis being zero according to the detection data comprises:

- obtaining a plurality of sets of detection data on the magnetic field intensity variation at the detection position during rotation of the magnetic ball around the first axis;
- obtaining the magnetic field intensity component in the direction of the second axis for each set of detection data according to the detection data; and
- determining whether the magnetic field intensity component in the direction of the second axis is zero to obtain the zero point position P0 with the magnetic field intensity component in the direction of the second axis being zero.

Preferably, obtaining a zero point position $P_0$ of the magnetic ball with a magnetic field intensity component in the direction of a second axis being zero according to the detection data comprises:

- obtaining the position with the magnetic field component in the direction of the second axis being close to zero as the near-zero point position $P_1$ according to the detection data;
- using the near-zero point position $P_1$ as the zero point position $P_0$.

Preferably, obtaining a calibration position of the magnetic ball according to the detection data and the zero point position $P_0$ comprises:

- determining the data direction of the zero point position $P_0$ during the rotation of the magnetic ball around the first axis by the first angle;
- obtaining a first calibration position $V_0$ and a second calibration position $H_0$ of the magnetic ball according to the data direction of the zero point position $P_0$, the zero point position $P_0$, and the detection data.

Preferably, obtaining a calibration position of the magnetic ball according to the detection data and the zero point position $P_0$ further comprises:

when the data direction of the zero point position $P_0$ changes from positive to negative, the first calibration position $V_0=\alpha-90°$, and the second calibration position $H_0=-\beta$;

when the data direction of the zero point position $P_0$ changes from negative to positive, the first calibration position $V_0=\alpha+90°$, and the second calibration position $H_0=180°-\beta$, where the three-axis magnetic field components at the zero point position $P_0$ are ($b_{xi}$, $b_{yi}$, $b_{zi}$);

$\alpha$ is the angle of rotation when the magnetic ball reaching the zero point position $P_0$;

$\beta$ is the angle between the x-direction component $b_{xi}$ and the y-direction component $b_{yi}$ at the zero point position $P_0$.

According to another aspect of the present application, a magnetic ball calibration apparatus is provided, wherein the magnetic ball has magnetic poles along the main axis direction, comprising: a first driving unit, a three-axis magnetic sensor and a data processing unit;

the first driving unit is used to drive the magnetic ball to rotate around a first axis by a first angle;

the three-axis magnetic sensor is disposed adjacent to the magnetic ball to obtain detection data of the three-axis magnetic field components at the detection position during rotation of the magnetic ball; and the data processing unit is connected to the three-axis magnetic sensor for receiving the detection data of the three-axis magnetic field components, and obtaining the zero point position where the magnetic field intensity in a second axis direction is zero according to the detection data, and obtaining the calibration position of the magnetic ball according to the detection data and the zero point position $P_0$, and calibrating the magnetic ball according to the calibration position.

wherein, when the magnetic ball is located at the calibration position, the main axis coincides with the second axis;

the first axis is perpendicular to the second axis;

the three-axis magnetic field components comprise an X-axis magnetic field component, a Y-axis magnetic field component and a Z-axis magnetic field component;

the direction of the Z-axis magnetic field component coincides with the direction of the second axis, and the direction of the Y-axis magnetic field component coincides with that of the first axis.

Preferably, the first angle is greater than or equal to 180°, or is 200°.

Preferably, the data processing unit comprises:

a first processing unit, used for:

obtaining the magnetic field intensity component in the direction of the second axis for each set of detection data according to the detection data, and determining whether the magnetic field intensity component in the direction of the second axis is zero to obtain the zero point position $P_0$ with the magnetic field intensity component in the direction of the second axis being zero.

Preferably, the data processing unit comprises:

a first processing unit, used for:

obtaining the position with the magnetic field component in the direction of the second axis being close to zero as the near-zero point position $P_1$ according to the detection data;

using the near-zero point position $P_1$ as the zero point position $P_0$.

Preferably, the data processing unit comprises a second processing unit, used for: determining the data direction of the zero point position $P_0$ according to the detection data;

obtaining a first calibration position $V_0$ and a second calibration position $H_0$ of the magnetic ball according to the zero point position $P_0$, the data direction of the zero point position $P_0$, and the detection data.

Preferably, the first axis or the second axis passes through the three-axis magnetic sensor. The detection position comprises the position where the three-axis magnetic sensor is located.

According to the embodiments of the present application, the magnetic ball calibration apparatus and the magnetic ball calibration method provided, a three-axis magnetic sensor is used to determine the direction of the magnetic ball, which is simple to operate, and can conveniently, quickly, and accurately calibrate the magnetic ball, providing a precise basis for determining the attitude of the capsule endoscope.

According to the embodiments of the present application, the magnetic ball calibration apparatus and the magnetic ball calibration method provided, the calibration of the magnetic ball is achieved by detecting and analyzing the magnetic field values at the detection position, which is making the operation simple and convenient.

According to the embodiments of the present application, the magnetic ball calibration apparatus and the magnetic ball calibration method provided, automatic calibration may be achieved by rotating the magnetic ball by a certain angle, which is making the calibration process easy to control and avoiding errors introduced by manual operation.

According to the embodiments of the present application, the magnetic ball calibration apparatus and magnetic ball calibration method provided, the calibration position of the magnetic ball is determined based on the zero point position and the magnetic field values, avoiding errors due to insufficient data differentiation and improving the accuracy of magnetic ball calibration.

BRIEF DESCRIPTION OF THE DRAWINGS

The above and other objects, features and advantages of the application shall be made clearer by the following detailed description of embodiments of the present application with reference to the accompanying drawings, and in the accompanying drawings.

DETAILED DESCRIPTION

Figure 1:
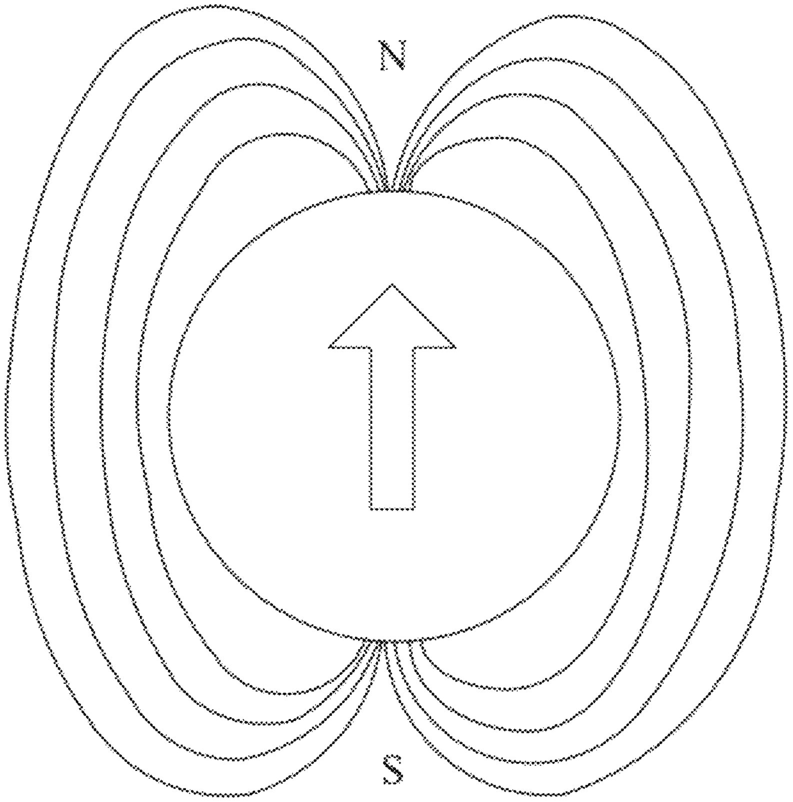
FIG. 1 shows a schematic diagram of a magnetic field distribution of a magnetic ball according to an embodiment of the present application.

Various embodiments of the present application will be described in more detail below with reference to the accompanying drawings. In the various accompanying drawings, the same elements are represented by the same or similar reference numerals. For clarity, the various parts of the accompanying drawings are not drawn to scale. In addition, some well-known parts may not be shown in the drawings.

Specific embodiments of the present application are described in further details below in conjunction with the accompanying drawings. Many specific details of the present application are described below, such as the structure, materials, dimensions, processing techniques, and techniques, of the components, in order to understand the present application more clearly. However, as may be understood by those skilled in the art, the present application may be implemented without following these particular details.

It should be understood that, when a layer or an area is referred to as being "Above" or "Over" another layer or another area in describing the structure of a component, it may refer to being directly on another layer or another area, or containing other layers or areas between it and another layer or another area. Also, if the component is turned over, the layer or area shall be "Under" or "Below" another layer or another area.

FIG. 1 shows a schematic diagram of a magnetic field distribution of a magnetic ball 10 according to an embodiment of the present application. As shown in FIG. 1, in an embodiment of the present application, the magnetic ball 10 comprises magnetic poles along the main axis direction (the magnetic field in a specific direction). The main axis coincides with the line connecting the N pole and S pole of the magnetic ball, which is a specific axis on the magnetic ball. According to an embodiment of the present application, the two ends of a certain diameter of the magnetic ball 10 are the N pole and S pole, respectively. The magnetic field distribution of the magnetic ball 10 is shown, for example, by the magnetic induction lines as in FIG. 1.

Figure 2:
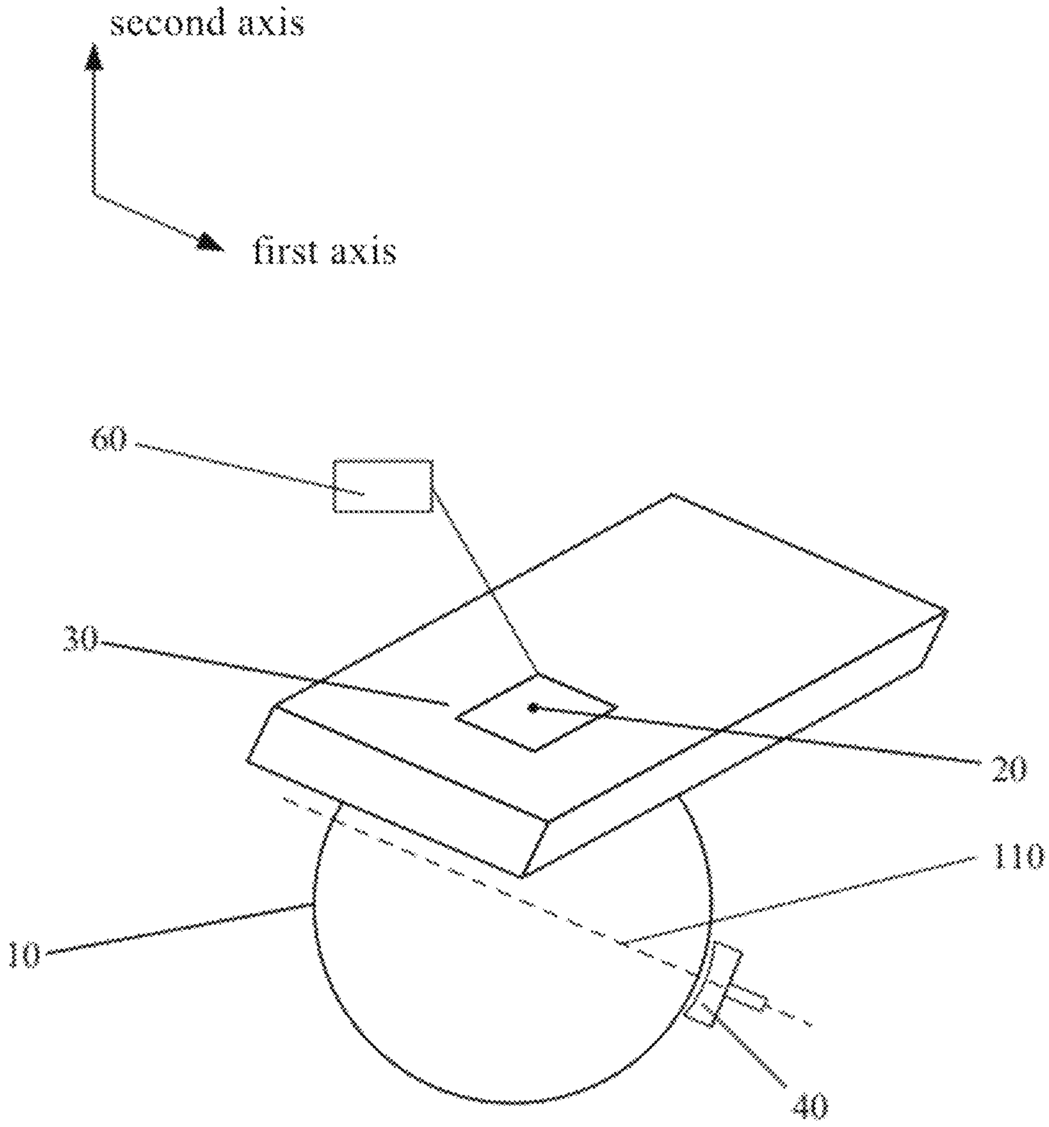
FIG. 2 shows a stereoscopic schematic diagram of a magnetic ball calibration apparatus according to a first embodiment of the present application.

FIG. 2 shows a stereoscopic schematic diagram of a magnetic ball calibration apparatus according to a first embodiment of the present application. As shown in FIG. 2, in one aspect, the embodiment of the present application provides a magnetic ball calibration apparatus, comprising a three-axis magnetic sensor 20, a first driving unit 40, and a data processing unit 60. The magnetic ball 10 comprises a first direction and a second direction, where the first direction is the direction in which the magnetic ball 10 rotates around the first axis 110, and the second direction is the direction in which the magnetic ball 10 rotates around the second axis 120.

The first driving unit 40 is used to drive the magnetic ball 10 to rotate in the first direction;

the three-axis magnetic sensor 20 is disposed adjacent to the magnetic ball 10 to obtain detection data of the three-axis magnetic field components during the rotation of the magnetic ball; and the data processing unit 60 is connected to the three-axis magnetic sensor 20 to receive the detection data of the three-axis magnetic field components, and to obtain a zero point position P0 where the magnetic field intensity component in the selected direction is zero at the detection location according to the detection data, and to obtain the calibration position of the magnetic ball according to the detection data and the zero point position P0, and to calibrate the magnetic ball according to the calibration position. The zero point position P0 not only includes the position information of that point but also includes the direction of data change at that point, etc.

Figure 6:
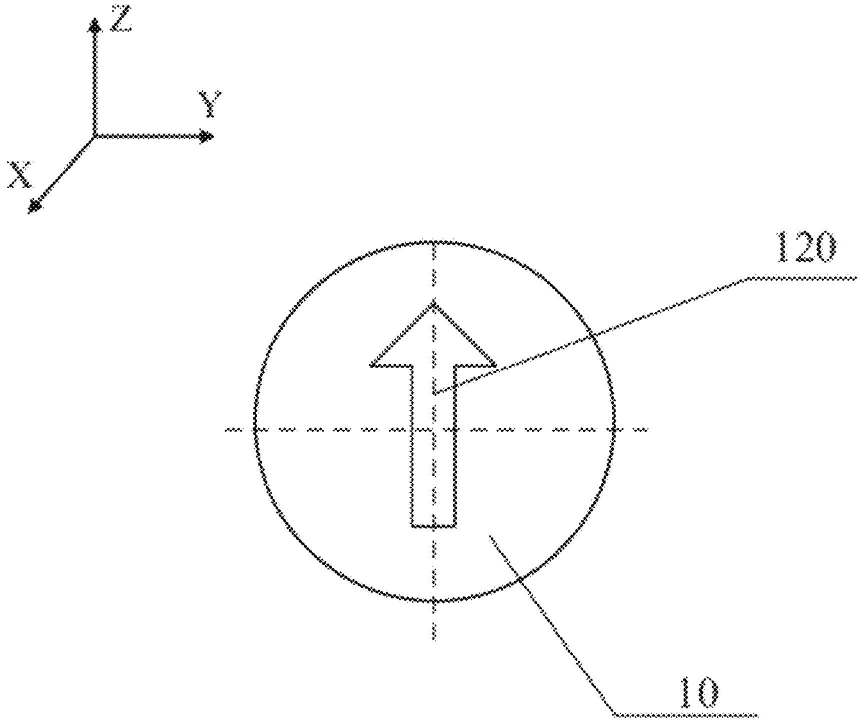
FIG. 6 shows a schematic diagram of the magnetic ball after calibration according to an embodiment of the present application.

Referring to FIG. 6, when the magnetic ball 10 is in the calibration position, the main axis coincides with the direction of the second axis. The first axis and the second axis are perpendicular to each other. The three-axis magnetic field components comprise an X-axis magnetic field component, a Y-axis magnetic field component, and a Z-axis magnetic field component. The direction of the Z-axis magnetic field component coincides with the direction of the second axis. The direction of the Y-axis magnetic field component coincides with the direction of the first axis.

Specifically, the magnetic ball 10 can rotate around the first axis 110 and/or the second axis 120 (i.e., rotate in the first direction and/or the second direction). During the movement of the magnetic ball 10, the first axis 110 maintains a fixed attitude relative to the second axis 120 (for example, a fixed angle). Optionally, the position of the rotation shaft of the first axis 110 and/or the second axis 120 is fixed, or the rotation shaft is fixedly installed in the capsule endoscope system. Preferably, both the first axis 110 and the second axis 120 pass through the center of the magnetic ball 10, and the first axis 110 is perpendicular to the second axis 120. Accordingly, a three-axis (three-dimensional rectangular coordinate system) is established. Optionally, in this coordinate system, the line where the first axis 110 is located is configured as the Y-axis, and the center of the magnetic ball 10 is configured as the zero point. The three-axis magnetic field components are the magnetic field components on the three axes of the three-dimensional rectangular coordinate system.

Optionally, the three-axis magnetic field components are determined by the direction of the three-axis magnetic sensor 20 itself, specifically by the chip (not shown) of the sensor. The three-axis directions of the three-axis magnetic field components are: vertically upward from the plane of the chip as the $Z_1$ axis, $X_1$ axis and $Y_1$ axis parallel to the plane of the chip. The directions of the $X_1$ axis, $Y_1$ axis, and $Z_1$ axis of the chip correspond to the directions of the X-axis, Y-axis, and Z-axis in the three-dimensional rectangular coordinate system. Later, the three-axis magnetic field components are described using the three axes of the three-dimensional rectangular coordinate system, i.e., the three-axis magnetic field components comprise an X-axis magnetic field component, a Y-axis magnetic field component, and a Z-axis magnetic field component. The direction of the Z-axis magnetic field component coincides with the direction of the second axis 120. The direction of the Y-axis magnetic field component coincides with the direction of the first axis 110.

In this embodiment, when calibrating the magnetic ball 10, the first driving unit 40 drives the magnetic ball 10 to rotate around the first axis 110 (in the first direction) by a first angle. Optionally, the first driving unit 40 drives the magnetic ball 10 to rotate around the first axis 110. Additionally, the magnetic ball calibration apparatus also comprises a three-axis magnetic sensor 20 placed adjacent to the magnetic ball 10 to detect the magnetic field intensity of the magnetic ball 10, especially the magnetic field intensity change during the rotation of the magnetic ball 10.

More specifically, the three-axis magnetic sensor 20 is located directly above the magnetic ball 10 (i.e., at the top of the magnetic ball 10 along the Z-axis) to detect the magnetic field intensity of the magnetic ball 10 in the three-axis direction (i.e., the magnetic field intensity in each direction in three-dimensional space). In other embodiments of the present application, the three-axis magnetic sensor 20 may also be disposed in other positions, as long as it can accurately obtain the magnetic field intensity data of the magnetic ball 10 during the rotation.

In one embodiment, the first driving unit 40 may be located on the side of the magnetic ball 10 (for example, on both sides of the magnetic ball 10) to drive the magnetic ball 10 to rotate around the first axis 110.

The three-axis magnetic sensor 20 is disposed adjacent to the magnetic ball 10 to detect the detection data of the three-axis magnetic field components during the rotation of the magnetic ball 10 (for example, detecting the magnetic field intensity of the magnetic ball 10 in each direction in three-dimensional space). In an embodiment of the present application, the distance between the three-axis magnetic sensor 20 and the surface of the magnetic ball 10 can be adjusted based on the magnetic field intensity of the magnetic ball 10 and/or the sensitivity of the three-axis magnetic sensor 20. The present application does not further limit the distance between the three-axis magnetic sensor 20 and the outer surface of the magnetic ball 10, as long as the three-axis magnetic sensor 20 can accurately acquire the magnetic field intensity data of the magnetic ball 10. Further, in this embodiment, the first driving unit 40 may directly control the rotation of the magnetic ball 10, or may also control the rotation of the magnetic ball 10 through a transmission component (not shown), which is not elaborated further here.

For ease of installation and to improve measurement accuracy, in an optional embodiment, the first axis 110 or the second axis 120 passes through the three-axis magnetic sensor 20. In this case, the position where the three-axis magnetic sensor 20 is located can serve as the detection position.

The data processing unit 60 is connected to the three-axis magnetic sensor 20 to receive the detection data of the three-axis magnetic field components, and obtain the calibration position of the magnetic ball 10 according to the detection data changing with the rotation of the magnetic ball 10. The connection between the data processing unit 60 and the three-axis magnetic sensor 20 can be either a wired connection or a wireless connection. In one embodiment, the data processing unit 60 can be one or more processors.

In this embodiment, the data processing unit 60 comprises a first processing unit (not shown) and a second processing unit (not shown). The first processing unit is used to obtain the zero point position $P_0$ at a specific position where the magnetic field intensity in the Z-axis direction is zero according to the detection data. It should be noted that the zero point position $P_0$ obtained by the first processing unit is position information (or angle information). The second processing unit is used for determining the data direction of the zero point position $P_0$ according to the detection data. The second processing unit is used for obtaining a first calibration position $V_0$ and a second calibration position $H_0$ of the magnetic ball 10 according to the zero point position $P_0$, the data direction of the zero point position P0, and the detection data.

In a preferred embodiment of the present application, the installation positions of the three-axis magnetic sensor 20 and the first driving unit 40 are relatively fixed, facilitating the integrated design of the magnetic ball calibration apparatus. To simplify the structure of the capsule endoscope system, in the embodiment of the present application, the first driving unit 40 may be a driving component on the magnetic control device within the capsule endoscope system that drive the rotation of the magnetic ball 10.

In an optional embodiment of the present application, to support the three-axis magnetic sensor 20, a magnetic field plate 30 is arranged adjacent to the magnetic ball 10, and the three-axis magnetic sensor 20 is disposed on the magnetic field plate 30. The magnetic field plate 30 is used to mount the three-axis magnetic sensor 20, and the overall structure of the magnetic field plate 30 is flat, occupying little space, and it can comprehensively cover the magnetic ball 10, which facilitates flexible installation of the three-axis magnetic sensor 20 and helps to reduce the overall size of the device. In other embodiments of the present application, the magnetic field plate 30 may also be another structure that fixes the three-axis magnetic sensor 20, which is not elaborated further here.

In an optional embodiment of the present application, the magnetic ball calibration apparatus further comprises a readable storage medium (not shown) for storing data. The readable storage medium is connected to the data processing unit 60 and the three-axis magnetic sensor 20, respectively. Optionally, the readable storage medium is connected to the data processing unit 60 to store the data calculated by the data processing unit 60 and/or the data to be received by the data processing unit 60 (e.g., the detection data obtained by the three-axis magnetic sensor 20 and/or the motion data of the magnetic ball 10). Optionally, the readable storage medium is connected to the three-axis magnetic sensor 20 to store the detection data obtained by the three-axis magnetic sensor 20.

Figure 3:
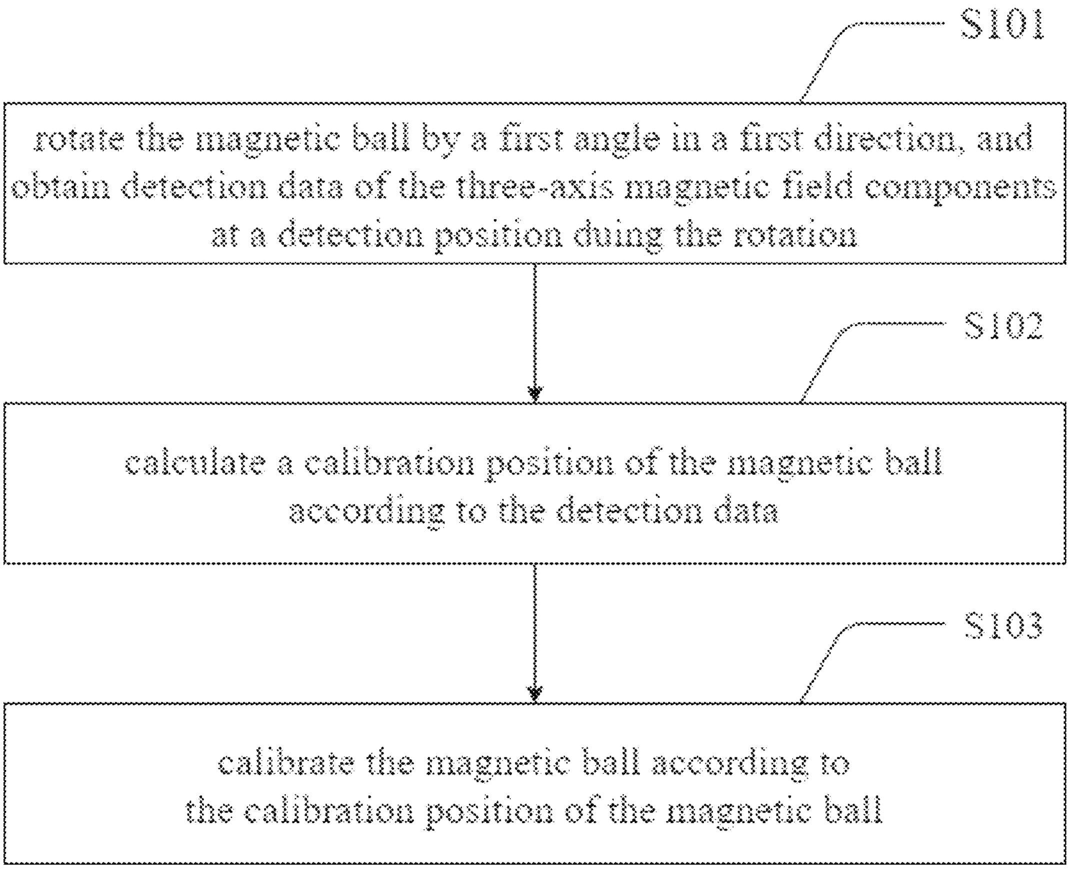
FIG. 3 shows a flowchart of a magnetic ball calibration method according to the first embodiment of the present application.

FIG. 3 shows a flowchart of a magnetic ball calibration method according to the first embodiment of the present application.

Referring to FIG. 2 and FIG. 3, the calibration method for the magnetic ball 10 according to the magnetic ball calibration apparatus of the first embodiment of the present application, comprises the following steps:

Step S101, rotating the magnetic ball 10 by a first angle in a first direction, and obtaining detection data of the three-axis magnetic field components at a detection position during the rotation process. The detection position refers to the set detection position, for example, the position of a detection device (for example, three-axis magnetic sensor), etc. Preferably, the first angle is greater than or equal to 180°. In a preferred embodiment of the present application, the first angle of rotation of the magnetic ball 10 is 200°, which ensures that the position of the magnetic ball 10 during rotation must include the zero point position $P_0$, while also preventing the excessive rotation of the magnetic ball 10 from introducing a large amount of data that would result in unnecessary computational load, thereby improving the efficiency of the magnetic ball calibration.

Step S102, calculating a calibration position of the magnetic ball 10 according to the detection data.

where, when the magnetic ball 10 is located at the calibration position, the magnetic polarization direction of the magnetic ball 10 coincides with the second axis 120, that is, the main axis of the magnetic ball coincides with the second axis 120.

Referring to FIG. 2, the first driving unit 40 drives the magnetic ball 10 to rotate around the first axis 110 by the first angle. During the rotation of the magnetic ball 10 around the first axis 110, the three-axis magnetic sensor 20 obtains the detection data of the three-axis magnetic field components at a detection position during the rotation. In this embodiment, the detection position, i.e. the position of the three-axis magnetic sensor 20, is taken as an example.

Further, the data processing unit 60 receives the obtained detection data of the three-axis magnetic field components, and calculates the calibration position of the magnetic ball 10 according to the detection data of the three-axis magnetic field components.

It is worth mentioning that in the present application, the three-axis magnetic sensor 20 may be disposed around the magnetic ball 10, and may be disposed at any position where changes in the magnetic field of the magnetic ball 10 can be accurately detected, and compensating by increasing or decreasing one or more deflection angles when calculating the angle. In the process of measuring the zero point position of the magnetic ball 10 mentioned above, the process of determining the zero point is still done by sensing the magnetic field changes of the magnetic ball 10 during rotation and processing them. The deflection angle can be obtained by a positional relationship between the three-axis magnetic sensor 20 and the rotation shaft of the magnetic ball 10.

It should be noted that the data processing unit 60 can obtain the calibration position of the magnetic ball 10 based on the detection data of the three-axis magnetic field components as the rotation angle of the magnetic ball changes during the rotation of the magnetic ball 10. In the case where the motion mode of the magnetic ball 10 is clear, that is, the rotation angle of the magnetic ball 10 and time satisfy a certain relationship, the data processing unit 60 can obtain the calibration position of the magnetic ball 10 according to changes in the detection data over time during the rotation process of the magnetic ball 10.

Step S103, calibrating the magnetic ball 10 according to the calibration position of the magnetic ball 10.

Rotating the magnetic ball 10 to the calibration position according to the calculated calibration position to complete the calibration.

After the steps of magnetic ball calibration method are completed, the magnetic ball 10, of which the current position has a deviation from the calibration position, can be corrected (calibrated), that is, rotating the magnetic ball 10 to the calibration position. For example, correcting the magnetic ball 10 so that its magnetization direction coincides with the first axis 110, or correcting the magnetic ball 10 so that its magnetization direction is perpendicular to the first axis 110 (that is, the magnetization direction coincides with the second axis 120).

Figure 4:
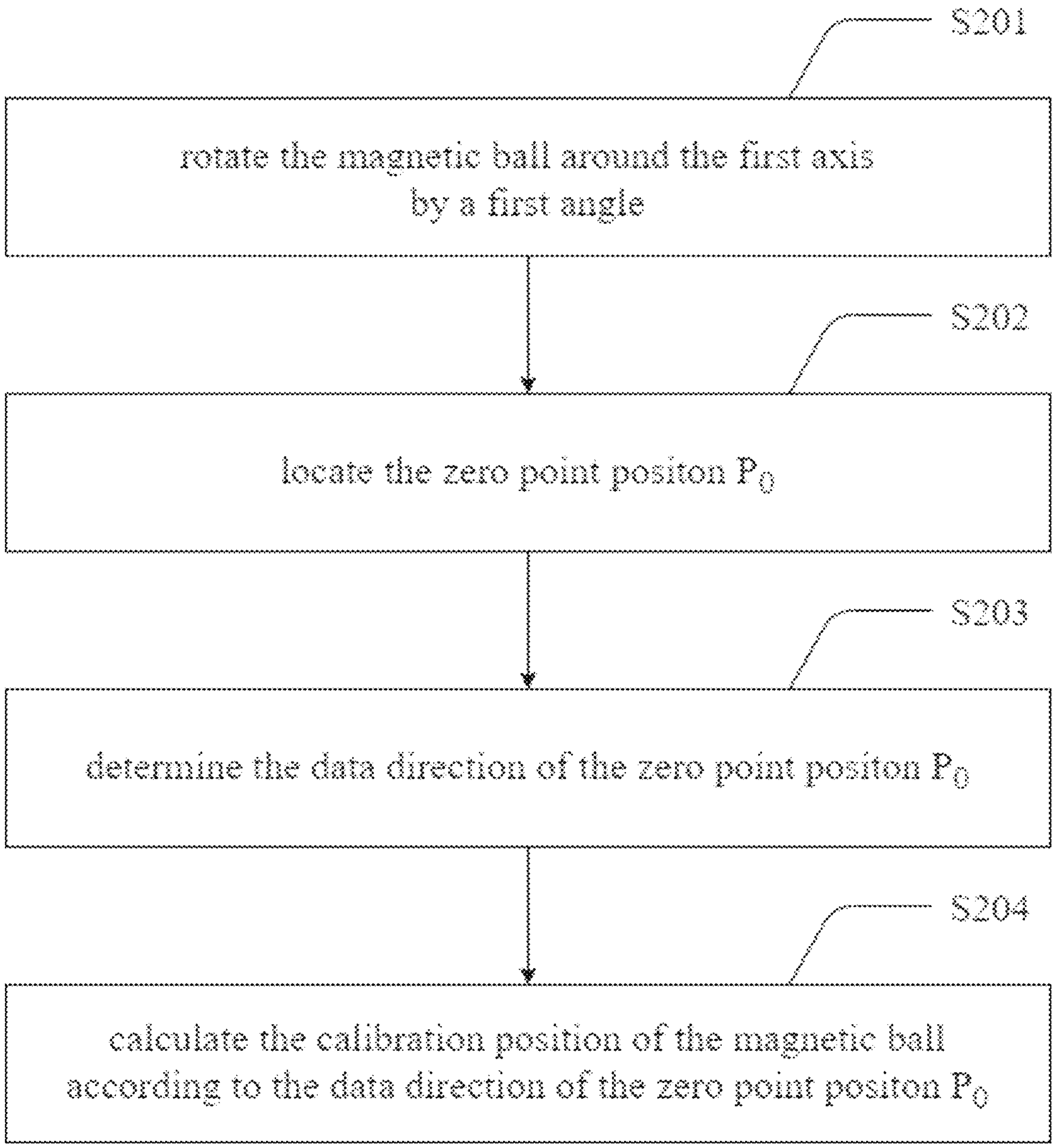
FIG. 4 shows a flowchart of the magnetic ball calibration method according to a second embodiment of the present application.

FIG. 4 shows a flowchart of the magnetic ball calibration method according to a second embodiment of the present application. As shown in FIG. 4, the magnetic ball calibration method of the second embodiment of the present application is a further improvement of the magnetic ball calibration method in the first embodiment.

As shown in FIG. 4, the second embodiment of the present application comprises the following steps:

Step S201, rotating the magnetic ball 10 around the first axis by the first angle.

The magnetic ball 10 rotates vertically, that is, the magnetic ball 10 rotates around the first axis 110 by the first angle, where the first angle is greater than or equal to 180°, for example, the first angle is 200°. This ensures that during the rotation of the magnetic ball 10, the zero point position can pass through the detection position set by the three-axis magnetic sensor 20.

Step S202, locating the zero point position $P_0$.

Obtaining the zero point position P0 of the magnetic ball 10 with a magnetic field intensity component in the direction of the second axis 120 being zero according to the detection data;

detecting and recording the variation in the magnetic field intensity at the detection position during the rotation of the magnetic ball 10 around the first axis 110, and recording a plurality of sets of detection data of the three-axis magnetic field components at the detection position during the rotation: $(b_{x0}, b_{y0}, b_{z0})$, $(b_{x1}, b_{y1}, b_{z1})$, . . . , $(b_{xn}, b_{yn}, b_{zn})$. Where, if the component value of the magnetic field in a selected direction is 0 in a set of detected data, the corresponding rotation position of the magnetic ball 10 is the zero point position $P_0$. Alternatively, the zero point position $P_0$ is the rotation position of the magnetic ball 10 when the three-axis magnetic sensor 20 at the detection position detects that the component of the magnetic field intensity in the selected direction is zero. In this embodiment, it is determined whether the component of the magnetic field intensity in the Z-axis direction is zero. The zero point position $P_0$ can reflect the angle at which the magnetic ball 10 has turned from the beginning to the position where the magnetic field intensity in the selected direction is zero. In other embodiments, the selected direction mentioned above can also be chosen from either the X-axis direction or the Y-axis direction based on practical selection.

However, in practical operation, due to the limitations of the measurement accuracy of the three-axis magnetic sensor 20, when the measurable value is 0, the magnetic induction intensity of the magnetic ball 10 in the selected direction is not necessarily 0, which means that the zero point position $P_0$ may not be accurately detected.

Accordingly, in the optional embodiment of the present application, locating the zero point position $P_0$ comprises:

detecting the near-zero point position $P_1$ of the magnetic field in the selected direction. Wherein, the near-zero point position $P_1$ is where the magnetic field component of the magnetic ball 10 in that direction is close to zero. Moreover, there is a positive or negative change in the measurement value of the three-axis magnetic sensor 20 at the near-zero point position $P_1$ and the measurement value at the next position below the near-zero point position $P_1$.

The zero point position $P_0$ is obtained based on the near-zero point position $P_1$. Optionally, in this embodiment, the near-zero point position $P_1$ can be selected as the zero point position $P_0$.

Preferably, the zero point position $P_0$ can also be calculated based on the near-zero point position $P_1$, for example, using interpolation to calculate the zero point position $P_0$, which is not elaborated here.

Step S203, determining the data direction of the zero point position $P_0$.

Specifically, as the magnetic ball 10 rotates, determining the date direction of the zero point position $P_0$ means, determining whether the change in the magnetic field intensity component in the Z-axis direction detected when the zero point position $P_0$ is detected is from positive to negative or from negative to positive.

Step S204, calculating the calibration position of the magnetic ball according to the data direction of the zero point position $P_0$ and the detection data.

In this embodiment, the calibration position comprises: the first calibration position $V_0$ and the second calibration position $H_0$. Wherein, the first calibration position $V_0$ determines the calibration position in the first direction (i.e., the direction in which the magnetic ball 10 rotates around the first axis 110); the second calibration position $H_0$ determines the calibration position in the second direction (i.e., the direction in which the magnetic ball 10 rotates around the second axis 120).

Figure 5:
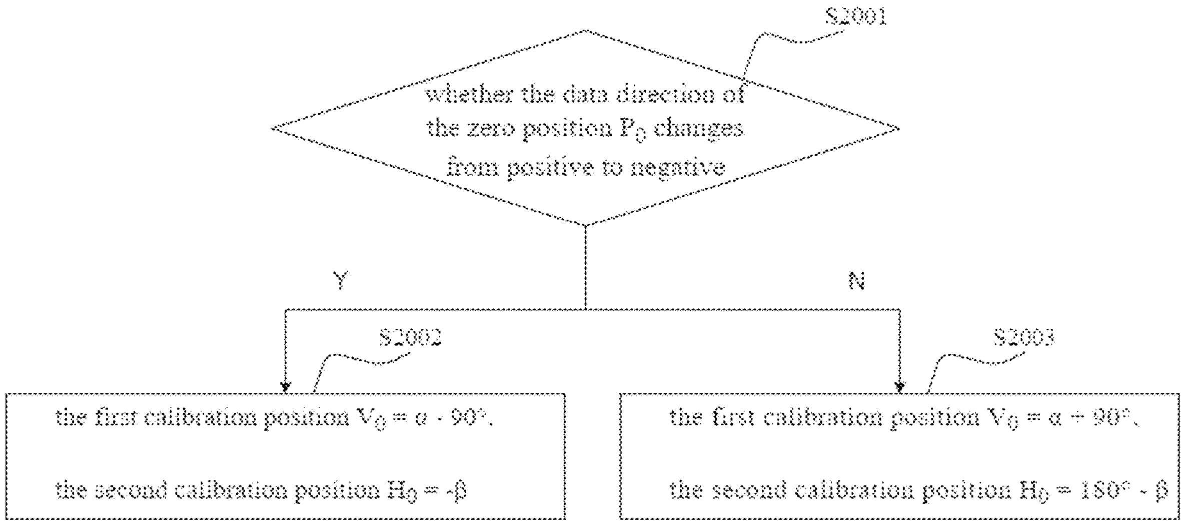
FIG. 5 shows a flowchart of obtaining a first calibration position and a second calibration position according to an embodiment of the present application.

As shown in FIG. 5, in an optional embodiment of the present application, the magnetic ball is controlled to rotate in a first direction by a first angle greater than 180°, followed by recording the three-dimensional magnetic field data ($b_{x0}$, $b_{y0}$, $b_{z0}$), ($b_{x1}$, $b_{y1}$, $b_{z1}$), . . . , ($b_{xn}$, $b_{yn}$, $b_{zn}$) obtained by the three-axis magnetic sensor 20 during the rotation of the magnetic ball, and detecting the position where the z-direction data of the magnetic field passes through the zero point, that is, the zero point position $P_0$.

The angle of rotation when the magnetic ball reaches the zero point position is $\alpha$. The angle range of $\alpha$ is, for example, the left-closed and right-open interval from 0 to $2\pi$.

The angle between the x-direction component $b_{xi}$ and the y-direction component $b_{yi}$ at the zero point position $P_0$ is $\beta$, where $\beta$=atan 2($b_{yi}$, $b_{xi}$). According to the numerical values of the x-direction component $b_{xi}$ and the y-direction component $b_{yi}$, $\beta$ can include the following situations:

when $b_{xi}>0$, $\beta=\arctan(b_{yi}/b_{xi})$;
when $b_{yi}>0$ and $b_{xi}<0$, $\beta=\arctan(b_{yi}/b_{xi})+\pi$;
when $b_{yi}\leq 0$ and $b_{xi}<0$, $\beta=\arctan(b_{yi}/b_{xi})-\pi$;
when $b_{yi}\geq 0$ and $b_{xi}=0$, $\beta=\pi/2$;
when $b_{yi}\leq 0$ and $b_{xi}=0$, $\beta=-\pi/2$.

where, the angle range of $\beta$ is, for example, the left-open and right-closed interval from $-\pi$ to $\pi$.

If the direction of the data change of the magnetic field intensity at the zero point position $P_0$ is from positive to negative, then the first calibration position of magnetic ball 10 (i.e., the zero point of magnetic ball 10 rotating around the first axis 110) is $V_0=\alpha-90°$. At this time, the second calibration position of the magnetic ball 10 (i.e., the zero point of the rotation of the magnetic ball 10 around the second axis 120) is $H_0=-\beta$.

If the direction of the data change of the magnetic field intensity at the zero point position $P_0$ is from negative to positive, then the first calibration position of magnetic ball 10 is $V_0=\alpha+90°$. At this time, the second calibration position of the magnetic ball 10 is $H_0=180°-\beta$.

The first processing unit is used to obtain the zero point position at a specific position where the magnetic field intensity in the Z-axis direction is zero according to the detection data. Wherein, the second processing unit is used to determine the data direction of the zero point position $P_0$ according to the detection data. Moreover, the second processing unit is further used for obtaining the first calibration position $V_0$ and the second calibration position $H_0$ of the magnetic ball 10 according to the zero point position $P_0$, the data direction of the zero point position $P_0$, and the detection data.

FIG. 6 shows a schematic diagram of the magnetic ball after calibration according to an embodiment of the present application. As shown in FIG. 6, after the calibration of the magnetic ball 10 according to an embodiment of the present application, the main axis of the magnetic ball 10 (i.e., the straight line on which the N magnetic pole and S magnetic pole are located) coincides with the second axis 120.

In this embodiment, the zero point position $P_0$ of the magnetic ball 10 is used as the calibration standard. The data distinction degree at this position is good, effectively avoiding the problem of insufficient calibration accuracy of the magnetic ball, reducing the impact of errors in practical measurements on the calibration results, and improving the calibration accuracy.

It should be noted that, relationship terms as described herein such as first and second are used only to distinguish one entity or operation from another, but do not necessarily require or imply any such actual relationship or sequence between these entities or operations. Moreover, the terms "include", "comprise" or any other variant thereof are intended to cover non-exclusive inclusion, so that a process, method, article or device that includes a series of elements includes not only those elements but also other elements that are not explicitly listed or further includes the elements inherent to such process, method, article or device. Without further limitation, the element limited by the statement "comprises a . . . " does not preclude the existence of another identical element in the process, method, article or equipment that includes said element.

In accordance with the embodiments of the present application as described above, these embodiments do not elaborate all details, and do not limit the disclosure to the specific embodiments described. Obviously, a plurality of modifications and changes can be made based on the above description. These embodiments have been selected and specifically described in this specification in order to better explain the principles and practical applications of the present application, so those skilled in the art can make good use of the present application and the modify based on the present application. The present application is limited only by the claims and their full scope and equivalents.

The invention claimed is:

1. A magnetic ball calibration method, comprising:

rotating a magnetic ball around a first axis by a first angle, and obtaining detection data of three-axis magnetic field components at a detection position during rotation, wherein the first angle is greater than or equal to 180°;

obtaining a zero point position P0 of the magnetic ball with a magnetic field intensity component in a direction of a second axis being zero according to the detection data;

obtaining a calibration position of the magnetic ball according to the detection data and the zero point position P0;

calibrating the magnetic ball according to the calibration position of the magnetic ball;

wherein, when the magnetic ball is located at the calibration position, a magnetic polarization direction of the magnetic ball coincides with the second axis;

the first axis is perpendicular to the second axis;

the three-axis magnetic field components comprise an X-axis magnetic field component, a Y-axis magnetic field component and a Z-axis magnetic field component;

a direction of the Z-axis magnetic field component coincides with the direction of the second axis, and a direction of the Y-axis magnetic field component coincides with that of the first axis.

2. The magnetic ball calibration method of claim 1, wherein obtaining the zero point position P0 of the magnetic ball with the magnetic field intensity component in the direction of the second axis being zero according to the detection data comprises:

obtaining a plurality of sets of detection data on a magnetic field intensity variation at the detection position during rotation of the magnetic ball around the first axis;

obtaining the magnetic field intensity component in the direction of the second axis for each set of detection data according to the detection data; and determining whether the magnetic field intensity component in the direction of the second axis is zero to obtain the zero point position P0 with the magnetic field intensity component in the direction of the second axis being zero.

3. The magnetic ball calibration method of claim 1, wherein obtaining the zero point position P0 of the magnetic ball with the magnetic field intensity component in the direction of the second axis being zero according to the detection data comprises:

obtaining a position with the magnetic field component in the direction of the second axis being close to zero as a near-zero point position P1 according to the detection data;

using the near-zero point position P1 as the zero point position P0.

4. The magnetic ball calibration method of claim 2, wherein obtaining the calibration position of the magnetic ball according to the detection data and the zero point position P0 comprises:

determining a data direction of the zero point position P0 during the rotation of the magnetic ball around the first axis by the first angle;

obtaining a first calibration position V0 and a second calibration position H0 of the magnetic ball according to the data direction of the zero point position P0, the zero point position P0, and the detection data.

5. The magnetic ball calibration method of claim 4, wherein obtaining the calibration position of the magnetic ball according to the detection data and the zero point position P0 further comprises:

when the data direction of the zero point position P0 changes from positive to negative, the first calibration position $V0=\alpha-90°$, and the second calibration position $H0=-\beta$;

when the data direction of the zero point position P0 changes from negative to positive, the first calibration position $V0=\alpha+90°$, and the second calibration position $H0=180°-\beta$, wherein the three-axis magnetic field components at the zero point position P0 are (bxi, byi, bzi);

$\alpha$ is an angle of rotation when the magnetic ball reaching the zero point position P0;

$\beta$ is an angle between an x-direction component bxi and a y-direction component byi at the zero point position P0.

6. A magnetic ball calibration apparatus, wherein a magnetic ball has magnetic poles along a main axis direction, comprising: a first driving motor, a three-axis magnetic sensor and a data processing unit;

the first driving motor is used to drive the magnetic ball to rotate around a first axis by a first angle;

the three-axis magnetic sensor is disposed adjacent to the magnetic ball to obtain detection data of three-axis magnetic field components at a detection position during rotation of the magnetic ball; and the data processing unit is connected to the three-axis magnetic sensor for receiving the detection data of the three-axis magnetic field components, and obtaining a zero point position P0 where a magnetic field intensity in a second axis direction is zero according to the detection data, and obtaining a calibration position of the magnetic ball according to the detection data and the zero point position P0, and calibrating the magnetic ball according to the calibration position;

wherein, when the magnetic ball is located at the calibration position, the main axis coincides with a second axis;

the first axis is perpendicular to the second axis;

the three-axis magnetic field components comprise an X-axis magnetic field component, a Y-axis magnetic field component and a Z-axis magnetic field component;

a direction of the Z-axis magnetic field component coincides with the direction of the second axis, and a direction of the Y-axis magnetic field component coincides with that of the first axis.

7. The magnetic ball calibration apparatus of claim 6, wherein the first angle is greater than or equal to 180°, or is 200°.

8. The magnetic ball calibration apparatus of claim 6, wherein the data processing unit comprises:

a first processing unit, used for:

obtaining the magnetic field intensity component in the direction of the second axis for each set of detection data according to the detection data, and determining whether the magnetic field intensity component in the direction of the second axis is zero to obtain the zero point position P0 with the magnetic field intensity component in the direction of the second axis being zero.

9. The magnetic ball calibration apparatus of claim 6, wherein the data processing unit comprises:

a first processing unit, used for:

obtaining a position with a magnetic field component in the direction of the second axis being close to zero as a near-zero point position P1 according to the detection data;

using the near-zero point position P1 as the zero point position P0.

10. The magnetic ball calibration apparatus of claim 8, wherein the data processing unit comprises a second processing unit, used for:

determining a data direction of the zero point position P0 according to the detection data;

obtaining a first calibration position V0 and a second calibration position H0 of the magnetic ball according to the zero point position P0, the data direction of the zero point position P0, and the detection data.

11. The magnetic ball calibration apparatus of claim 6, wherein the first axis or the second axis passes through the three-axis magnetic sensor; the detection position comprises a position where the three-axis magnetic sensor is located.

* * * * *